(12) United States Patent
Sajiki et al.

(10) Patent No.: US 10,442,834 B2
(45) Date of Patent: Oct. 15, 2019

(54) DEPROTECTION METHOD

(71) Applicant: AJINOMOTO CO., INC., Tokyo (JP)

(72) Inventors: Hironao Sajiki, Gifu (JP); Yasunari Monguchi, Gifu (JP)

(73) Assignee: AJINOMOTO CO., INC., Tokyo (JP)

( * ) Notice: Subject to any disclaimer, the term of this patent is extended or adjusted under 35 U.S.C. 154(b) by 280 days.

(21) Appl. No.: 14/873,517

(22) Filed: Oct. 2, 2015

(65) Prior Publication Data

US 2016/0024143 A1   Jan. 28, 2016

Related U.S. Application Data

(63) Continuation of application No. PCT/JP2014/059877, filed on Apr. 3, 2014.

(30) Foreign Application Priority Data

Apr. 4, 2013  (JP) .................................. 2013-078859

(51) Int. Cl.
| | | |
|---|---|---|
| *A61K 38/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07K 2/00* | (2006.01) | |
| *C07K 4/00* | (2006.01) | |
| *C07K 14/00* | (2006.01) | |
| *A61K 38/04* | (2006.01) | |
| *A61K 38/06* | (2006.01) | |
| *C07K 1/02* | (2006.01) | |
| *C07C 319/20* | (2006.01) | |
| *C07C 321/14* | (2006.01) | |
| *C07C 321/28* | (2006.01) | |
| *C07C 53/16* | (2006.01) | |
| *C07K 5/062* | (2006.01) | |
| *C07K 5/087* | (2006.01) | |
| *C07K 5/103* | (2006.01) | |

(52) U.S. Cl.
CPC ............... *C07K 1/02* (2013.01); *C07C 53/16* (2013.01); *C07C 319/20* (2013.01); *C07C 321/14* (2013.01); *C07C 321/28* (2013.01); *C07K 5/0606* (2013.01); *C07K 5/06026* (2013.01); *C07K 5/06069* (2013.01); *C07K 5/0812* (2013.01); *C07K 5/1008* (2013.01); *C07K 5/1013* (2013.01); *Y02P 20/55* (2015.11)

(58) Field of Classification Search
CPC ... C07C 319/20; C07C 321/14; C07C 321/28; C07C 53/16; C07K 1/02; C07K 5/06026; C07K 5/0606; C07K 5/0812; C07K 5/1008; C07K 5/1013
See application file for complete search history.

(56) References Cited

U.S. PATENT DOCUMENTS

| | | | |
|---|---|---|---|
| 4,730,076 | A | 3/1988 | Fujii et al. |
| 7,053,041 | B1 | 5/2006 | Brooks et al. |
| 7,319,099 | B2 | 1/2008 | Jolidon et al. |
| 7,605,163 | B2 | 10/2009 | Jolidon et al. |
| 2005/0209241 | A1 | 9/2005 | Jolidon et al. |
| 2008/0119486 | A1 | 5/2008 | Jolidon et al. |
| 2010/0087466 | A1 | 4/2010 | Sturgess et al. |

FOREIGN PATENT DOCUMENTS

| | | |
|---|---|---|
| CN | 101921309 A | 12/2010 |
| JP | 56-81545 A | 7/1981 |
| JP | 62-145100 A | 6/1987 |
| JP | 2002-515036 A | 5/2002 |
| JP | 2007-501820 A | 2/2007 |
| JP | 2009-96740 A | 5/2009 |
| JP | 2010-126454 A | 6/2010 |
| JP | 2011-105648 A | 6/2011 |

OTHER PUBLICATIONS

Tsuda Y and Okada Y "Part Two Amino Acid Coupling Chemistry Solution-Phase Peptide Synthesis" from Amino Acids, Peptides and Proteins in Organic Chemistry. vol. 3—Buliding Blocks, Catalysis and Coupling Chemistry. Edited by Hughes A. 2011. p. 203-251.*
Lawrence S. Amines: Synthesis, Properties and Applications. p. 238. Published 2007.*
Giordano C et al. "Synthesis, conformation and biologically activity of centrally modified pseudopeptide analogs of For-Met-Leu-Phe-OMe" Amino Acids 33:477-487. Published 2007.*
Patil N "Protecting Group Strategies—Heterogenous Catalysis" NCL Presentation. (Year: 2012).*
International Search Report dated May 13, 2014 in PCT/JP2014/059877 (with English language translation).

(Continued)

*Primary Examiner* — Christina Bradley
*Assistant Examiner* — Zachary J Miknis
(74) *Attorney, Agent, or Firm* — Oblon, McClelland, Maier & Neustadt, L.L.P.

(57) ABSTRACT

The present invention provides a method of efficiently deprotecting a protected organic compound by catalytic hydrogenation. Specifically, the present invention provides a method of deprotecting an organic compound having at least one functional group selected from the group consisting of a carboxy group, an amino group and a hydroxy group, which is protected by a protecting group represented by the formula (I):

$$R^1\text{—}C(R^2)(R^3)\text{-}L^1\text{-} \quad (I)$$

[wherein $R^1$ is an aryl group optionally having substituent(s), $R^2$ and $R^3$ are each independently, a hydrogen atom or an aryl group optionally having substituent(s), and $L^1$ is a single bond, —O—CO— or —O—CH$_2$—], comprising hydrogenation in the presence of a metal catalyst and halogenated acetic acid.

9 Claims, No Drawings

Specification includes a Sequence Listing.

(56) References Cited

OTHER PUBLICATIONS

Akinori Mori, et al., "Chemoselective Hydrogenation using Sulfur Catalyst Poison" The Annual Proceedings of Gifu Pharmaceutical University, vol. 57, 2008, pp. 45-53 (with English Abstract).
"Removal of N-Benzyloxycarbonyl from Sulfer-Containing Peptides by Catalytic Hydrogenation in Liquid Ammonia: O-tert-BUTYL-L-Seryl-S-tert-BUTYL-L-Cysteine tert-BUTYL Ester" Organic Syntheses, Coll., vol. 6, 1988, 8 Pages.
Cesare Giordano, et al., "B-Peptido sulfonamides: for-Met-Leu-Phe-OMe analogues containing taurine and chiral B-aminoethanesulfonic acid residues" IL FARMACO, vol. 59, 2004, pp. 953-963.
C. Giordano, et al., "Synthesis, conformation and biological activity of centrally modified pseudopeptidic analogues of For-Met-Leu-Phe-OMe" Amino Acids, vol. 33, 2007, pp. 477-487.
Karina Thorn, et al., "The tandem chain extension aldol reaction used for synthesis of ketomethylene tripeptidomimetics targeting hPEPT1" Bioorganic & Medicinal Chemistry Letters, vol. 21, 2011, pp. 4597-4601.
Kirandeep Kaur, et al., "Synthesis, antimalarial, antileishmanial, antimicrobial, cytotoxicity, and methemoglobin (MetHB) formation activities of new 8-quinolinamines" Bioorganic & Medicinal Chemistry, vol. 15, 2007, pp. 915-930.
Xubo Hu, et al., "Peptidyl hydroxamic acids as methionine aminopeptidase inhibitors" Bioorganic & Medicinal Chemistry Letters, vol. 14, 2004, pp. 77-79.
Dinesh V. Patel, et al., "Retro-Inverso Tripeptide Renin Inhibitors" Bioorganic & Medicinal Chemistry Letters, vol. 2, No. 9, 1992, pp. 1089-1092.

\* cited by examiner

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Protected by t-butoxycarbonyl (Boc) group
<220> FEATURE:
<221> NAME/KEY: MOD_RES
<222> LOCATION: (1)..(1)
<223> OTHER INFORMATION: Modified by benzyl (Bn) group
<220> FEATURE:
<221> NAME/KEY: MOD_RES
<222> LOCATION: (5)..(5)
<223> OTHER INFORMATION: Modified by nitro (NO2) group
<220> FEATURE:
<221> NAME/KEY: MOD_RES
<222> LOCATION: (6)..(6)
<223> OTHER INFORMATION: Modified by benzyl (Bn) group
<220> FEATURE:
<221> NAME/KEY: MOD_RES
<222> LOCATION: (9)..(9)
<223> OTHER INFORMATION: Terminated by oxybenzyl (OBn) group
```

```
<400> SEQUENCE: 1

Ser Ala Leu Leu Arg Ser Ile Pro Ala
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Protected by benzyloxymethyl (Bom) group
<220> FEATURE:
<221> NAME/KEY: MOD_RES
<222> LOCATION: (3)..(3)
<223> OTHER INFORMATION: Modified by nitro (NO2) group
<220> FEATURE:
<221> NAME/KEY: MOD_RES
<222> LOCATION: (5)..(5)
<223> OTHER INFORMATION: Protected by benzyloxymethyl (Bom) group
<220> FEATURE:
<221> NAME/KEY: MOD_RES
<222> LOCATION: (6)..(6)
<223> OTHER INFORMATION: Terminated by amino (NH2) group

<400> SEQUENCE: 2

His Val Arg Gln His Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Ser Ala Leu Leu Arg Ser Ile Pro Ala
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

His Val Arg Gln His Gly
1               5
```

DEPROTECTION METHOD

CROSS REFERENCES TO RELATED APPLICATIONS

This application is a continuation of International Patent Application No. PCT/JP2014/059877, filed on Apr. 3, 2014, and claims priority to Japanese Patent Application No. 2013-078859, filed on Apr. 4, 2013, all of which are incorporated herein by reference in their entireties.

BACKGROUND OF THE INVENTION

Field of the Invention

The present invention relates to a method of deprotecting, by catalytic hydrogenation, an organic compound having a functional group protected by a protecting group.

Discussion of the Background

In the field of organic synthesis, a method of protecting a functional group by a protecting group and a method of deprotection of the protecting group are frequently used, and improvement of the reaction efficiency thereof has been desired. A benzyl group (Ph-$CH_2$—, abbreviation Bn) and a benzhydryl group ($Ph_2$-CH—) are frequently used as a protecting group for carboxy group, amino group and hydroxy group, further, a trityl group ($Ph_3$-C—, abbreviation Tr) is frequently used as a protecting group for carboxy group and amino group, a benzyloxycarbonyl group (Ph-$CH_2$O—CO—, abbreviation Cbz) is frequently used as a protecting group for amino group and hydroxy group, a 9-phenylfluorenyl group represented by the following formula is frequently used as a protecting group for amino group, and a benzyloxymethyl group (Ph-$CH_2$O—$CH_2$—, abbreviation Bom) is frequently used as a protecting group for the amino group of an imidazole ring possessed by histidine and the like.

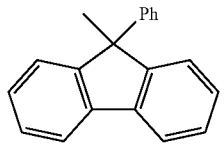 [SMILES: CC1(c2ccccc2)c2ccccc2-c2ccccc21]

A functional group protected by the aforementioned protecting group containing a structure represented by the formula: Ar—C— wherein Ar is an aryl group) (hereinafter sometimes to be abbreviated as "benzyl-type protecting group") is generally deprotected by catalytic hydrogenation using a metal catalyst (e.g., palladium catalyst, platinum catalyst etc.) under a hydrogen atmosphere. In this deprotection, it is considered that (1) first, a benzyl-type protecting group is trapped on a surface of the metal catalyst by an interaction between an aryl group and a metal catalyst, (2) then, cleavage of the benzyl-type protecting group and the functional group (e.g., carboxy group) proceeds due to catalytic hydrogenation on the surface of the metal catalyst.

The catalyst activity of a metal catalyst is markedly impaired by a catalyst poison present in situ. As such catalyst poison, a sulfur-containing organic compound is typical. Therefore, it is generally difficult to deprotect, by catalytic hydrogenation, a sulfur-containing organic compound having a functional group protected by a benzyl-type protecting group.

Non-patent document 1 describes that, in catalytic hydrogenation (metal catalyst: palladium carbon) of a substrate having an amino group protected by Cbz and a double bond, selective catalytic hydrogenation of the double bond alone is performed by adding diphenylsulfide in situ, without deprotecting Cbz.

Non-patent document 2 describes deprotection of Cbz, as shown in the following formula, by refluxing a sulfur-containing peptide having the N-terminus protected by Cbz together with palladium black and triethylamine in dimethylacetamide (DMAC) and liquid ammonia under a hydrogen stream. However, in the method described in non-patent document 2, an excess amount of palladium black is used in about 5 equivalents or 15 equivalents relative to the substrate to avoid an influence of catalyst poison.

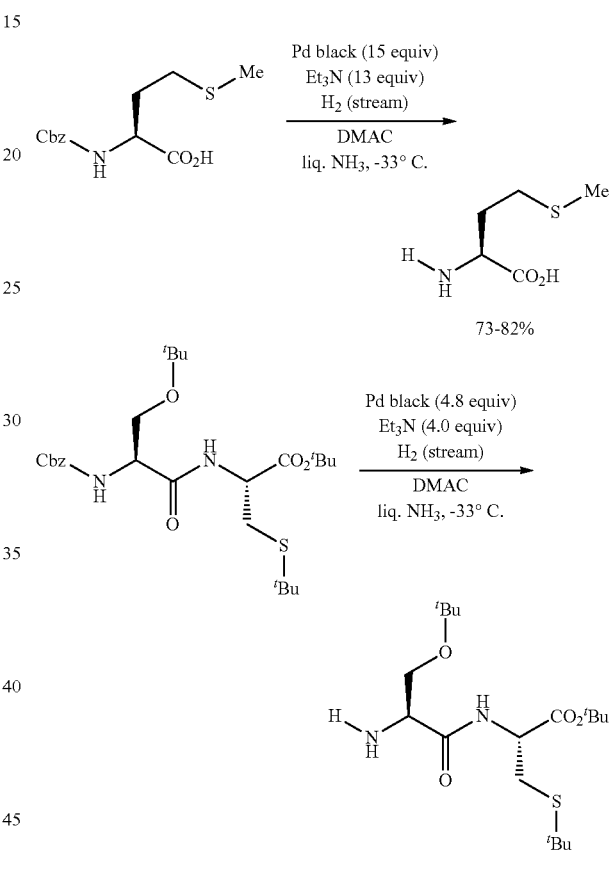

PRIOR ART DOCUMENTS

Non-Patent Documents non-patent document 1: Mori and Sajiki, Annual Report of Gifu Pharmaceutical University, Vol. 57, 45-53 (2008)
non-patent document 2: Meinhofer, J. et. al, Org. Synth, Coll. Vol. 6. 1988, 252

SUMMARY OF THE INVENTION

Problems to be Solved by the Invention

An object of the present invention is to improve the reaction efficiency of deprotection of a benzyl-type protecting group by catalytic hydrogenation. Furthermore, an object of the present invention is to provide a method of deprotecting, by catalytic hydrogenation, a sulfur-containing organic compound having a functional group protected by a benzyl-type protecting group.

Means of Solving the Problems

The present inventors have conducted intensive studies in an attempt to achieve the above-mentioned object and found that catalytic hydrogenation of an organic compound having a functional group protected by a benzyl-type protecting group, in the presence of a halogenated acetic acid and a metal catalyst under a hydrogen atmosphere markedly improves the efficiency of deprotection reaction, and further, suppresses the action of catalyst poison of the sulfur-containing organic compound to the metal catalyst, and can deprotect the sulfur-containing organic compound by catalytic hydrogenation, which resulted in the completion of the present invention. That is, the present invention includes the following.

[1] A method of deprotecting a sulfur-containing peptide containing at least one functional group selected from the group consisting of a carboxy group, an amino group, and a hydroxy group,
wherein said peptide:
(1) is protected by a protecting group represented by formula (I):

$$R^1\!-\!C(R^2)(R^3)\!-\!L^1\!-\qquad\qquad(I)$$

wherein $R^1$ is an aryl group optionally having one or more substituent(s), $R^2$ and $R^3$ are each, independently, a hydrogen atom or an aryl group optionally having one or more substituent(s), and $L^1$ is a single bond, —O—CO— or —O—CH$_2$—; and
(2) contains at least one sulfur-containing amino acid residue selected from the group consisting of methionine, cystine with protected sulfanyl group, and cystine,
wherein said method comprises subjecting said peptide to hydrogenation in the presence of a metal catalyst and a halogenated acetic acid.

[2] The method of the aforementioned [1], wherein said halogenated acetic acid is at least one member selected from the group consisting of trichloroacetic acid, dichloroacetic acid, monochloroacetic acid, trifluoroacetic acid, difluoroacetic acid, and monofluoroacetic acid.

[3] The method of the aforementioned [1], wherein said hydrogenation is conducted in the presence of trifluoroacetic

[4] The method of the aforementioned [1], wherein said hydrogenation is conducted in the presence of said halogenated acetic acid in an amount of not less than 1 mol per 1 mol of total sulfur atom contained in said sulfur-containing peptide.

[5] The method of the aforementioned [1], wherein said metal catalyst is at least one member selected from the group consisting of a nickel catalyst, a copper catalyst, a ruthenium catalyst, a palladium catalyst, a rhodium catalyst, and a platinum catalyst.

[6] The method of the aforementioned [1], wherein said hydrogenation is conducted in the presence of a palladium catalyst.

[7] The method of the aforementioned [6], wherein said hydrogenation is conducted in the presence of palladium carbon.

[8] The method of the aforementioned [1], wherein $R^1$ is a phenyl group optionally having one or more substituent(s).

[9] The method of the aforementioned [1], wherein said protecting group is selected from the group consisting of:
a benzyl group optionally having one or more substituent(s),
a benzhydryl group optionally having one or more substituent(s),
a trityl group optionally having one or more substituent(s),
a 9-phenylfluorenyl group optionally having one or more substituent(s),
a benzyloxycarbonyl group optionally having one or more substituent(s), and
a benzyloxymethyl group optionally having one or more substituent(s).

[10] The method of the aforementioned [1], wherein said protecting group is selected from the group consisting of:
a benzyl group optionally having one or more substituent(s),
a benzyloxycarbonyl group optionally having one or more substituent(s), and
a benzyloxymethyl group optionally having one or more substituent(s).

[11] A method of producing a sulfur-containing peptide, comprising the method of the aforementioned [1].

[12] A method of producing a sulfur-containing peptide, comprising:
(a) reacting:
(i) a free amino group of an amino acid having a carboxy group protected by a protecting group or a first peptide having a C-terminus protected by a protecting group with
(ii) a free carboxy group of an amino acid having an amino group protected by a protecting group to obtain a second peptide; and
(b) deprotecting any C-terminus and N-terminus, which are protected by a protecting group, of said second peptide, to obtain said peptide,
wherein said peptide contains at least one functional group selected from the group consisting of a carboxy group, an amino group, and a hydroxy group, which is protected by a protecting group represented by formula (I):

$$R^1\!-\!C(R^2)(R^3)\!-\!L^1\!-\qquad\qquad(I)$$

wherein $R^1$ is an aryl group optionally having one or more substituent(s), $R^2$ and $R^3$ are each, independently, a hydrogen atom or an aryl group optionally having one or more substituent(s), and $L^1$ is a single bond, —O—CO— or —O—CH$_2$—; and
said peptide contains at least one sulfur-containing amino acid residue selected from the group consisting of methionine, cysteine with protected sulfanyl group, and cystine, and
wherein said method further comprises subjecting said second peptide to hydrogenation in the presence of a metal catalyst and a halogenated acetic acid.

[13] The method of the aforementioned [12], wherein said halogenated acetic acid is at least one member selected from the group consisting of trichloroacetic acid, dichloroacetic acid, monochloroacetic acid, trifluoroacetic acid, difluoroacetic acid, and monofluoroacetic acid.

[14] The method of the aforementioned [12], wherein said hydrogenation is conducted in the presence of trifluoroacetic acid.

[15] The method of the aforementioned [12], wherein said hydrogenation is conducted in the presence of said halogenated acetic acid in an amount of not less than 1 mol per 1 mol of total sulfur atom contained in said sulfur-containing peptide.

[16] The method of the aforementioned [12], wherein said metal catalyst is at least one member selected from the group consisting of a nickel catalyst, a copper catalyst, a ruthenium catalyst, a palladium catalyst, a rhodium catalyst, and a platinum catalyst.

[17] A method of producing a peptide, comprising:
(a) reacting:
(i) a free amino group of an amino acid having a carboxy group protected by a protecting group or a first peptide having the C-terminus protected by a protecting group with
(ii) a free carboxy group of an amino acid having an amino group protected by a protecting group to obtain a second peptide;
(b) deprotecting the protected N-terminus of said second peptide, to obtain a third peptide containing an unprotected amino group;
(c) repeating step (a) and step (b) as necessary; and
(d) deprotecting all of the C-terminus and N-terminus, which are protected by a protecting group, of said third peptide, to obtain said peptide,
wherein said peptide contains at least one functional group selected from the group consisting of a carboxy group, an amino group, and a hydroxy group, which is protected by a protecting m group represented by formula (I):

wherein $R^1$ is an aryl group optionally having one or more substituent(s), $R^2$ and $R^3$ are each, independently, a hydrogen atom or an aryl group optionally having one or more substituent(s), and $L^1$ is a single, bond, —O—CO— or —O—CH$_2$—; and
said peptide contains at least one sulfur-containing amino acid residue selected from the group consisting of methionine, cysteine with protected sulfanyl group, and cystine, and
wherein said method further comprises subjecting said peptide to hydrogenation in the presence of a metal catalyst and a halogenated acetic acid.

[18] The method of the aforementioned [17], wherein said halogenated acetic acid is at least one member selected from the group consisting of trichloroacetic acid, dichloroacetic acid, monochloroacetic acid, trifluoroacetic acid, difluoroacetic acid, and monofluoroacetic acid.

[19] The method of the aforementioned [17], wherein said hydrogenation is conducted in the presence of trifluoroacetic acid.

[20] The method of the aforementioned [17], wherein said hydrogenation is conducted in the presence of said halogenated acetic acid in an amount of not less than 1 mol per 1 mol of total sulfur atom contained in said sulfur-containing peptide.

Effect of the Invention

According to the method of the present invention using a halogenated acetic acid, the reaction efficiency of deprotection, by catalytic hydrogenation, of an organic compound having at least one kind of a functional group selected from the group consisting of a carboxy group, an amino group and a hydroxy group, which is protected by a benzyl-type protecting group (hereinafter sometimes to be abbreviated as "protected functional group") (hereinafter sometimes to be abbreviated "protected organic compound") is improved. In the method described in the aforementioned non-patent document 2, to avoid an influence of catalyst poison, an excess metal catalyst is used to deprotect a sulfur-containing organic compound having an amino group protected by Cbz. Using the method of the present invention, a protected sulfur-containing organic compound can be deprotected by catalytic hydrogenation even without using an excess metal catalyst.

DETAILED DESCRIPTION OF THE PREFERRED EMBODIMENTS

[Organic Compound]
In the method of the present invention, an organic compound having a protected functional group is deprotected by catalytic hydrogenation in the presence of a halogenated acetic acid. Since the deprotection method of the present invention is performed in the presence of halogenated acetic acid, when the sulfur-containing organic compound has a protecting group (e.g., t-butoxycarbonyl group (Boc)) that can be removed by an acid, the protecting group can also be removed together with the benzyl-type protecting group.

In the present invention, the benzyl-type protecting group is represented by the formula (I):

[wherein $R^1$ is an aryl group optionally having substituent(s), $R^2$ and $R^3$ are each independently a hydrogen atom or an aryl group optionally having substituent(s), and $L^1$ is a single bond, —O—CO— or —O—CH$_2$—.]

In the following, the benzyl-type protecting group represented by the formula (I) is sometimes abbreviated as "protecting group (I)".

Examples of the aryl group include phenyl group, 1-naphthyl group, 2-naphthyl group, 2-anthryl group, phenanthryl group and the like. Of these, phenyl group is preferable. The aryl groups for $R^2$ and $R^3$ in the formula (I) may be bonded to each other. A group formed by the aryl groups of $R^2$ and $R^3$ bonded to each other is preferably a fluorenyl group.

The number and kind of the substituent that the aryl group optionally has are not particularly limited. The number of the substituents is generally an integer of 0-5, preferably 0-3, more preferably 0 or 1. More preferably, the aryl group does not have a substituent. Examples of the substituent include nitro group, halogen atom (fluorine, chlorine, bromine or iodine), aliphatic hydrocarbon group (e.g., alkyl group, alkenyl group, alkynyl group) and the like. The aliphatic hydrocarbon group may be any of linear, branched chain and cyclic. Furthermore, hydrogen atom of the aliphatic hydrocarbon group is optionally substituted by a substituent such as halogen atom and the like, and methylene chain (—CH$_2$—) thereof is optionally substituted by oxygen atom (—O—) and/or carbonyl group (—CO—). Of the aliphatic hydrocarbon groups wherein methylene chain is substituted by oxygen atom, alkoxy group is preferable. The alkyl group contained in the alkoxy group may be any of linear, branched chain and cyclic. Also, hydrogen atom of the alkoxy group is also optionally substituted by a substituent such as halogen atom and the like. The carbon number of the aliphatic hydrocarbon group and the alkoxy group is generally an integer of 1-10, preferably 1-6, more preferably 1-4.

The protecting group (I) is preferably the formula (I) wherein $R^1$ is a phenyl group optionally having substituent(s). Explanation of the kind and number of the substituent that the phenyl group optionally has is the same as that of the aforementioned aryl group.

Examples of the protecting group (I) wherein $R^1$ is a phenyl group optionally having substituent(s) include (1) a benzyl group optionally having substituent(s) (wherein $R^1$ is a phenyl group optionally having substituent(s), $R^2$ and $R^3$ are each a hydrogen atom, and $L^1$ is a single bond),
(2) a benzhydryl group optionally having substituent(s) (wherein $R^1$ and $R^2$ are each a phenyl group optionally having substituent(s), $R^3$ is a hydrogen atom, and $L^1$ is a single bond),
(3) a trityl group optionally having substituent(s) (wherein $R^1$-$R^3$ are each a phenyl group optionally having substituent(s), and $L^1$ is a single bond),
(4) a 9-phenylfluorenyl group optionally having substituent(s) (wherein $R^1$ is a phenyl group optionally having substituent(s), $R^2$ and $R^3$ are each a phenyl group optionally having substituent(s), and they are bonded to form a fluorenyl group optionally having substituent(s), and $L^1$ is a single bond),
(5) a benzyloxycarbonyl group optionally having substituent(s) (wherein $R^1$ is a phenyl group optionally having substituent(s), $R^2$ and $R^3$ are each a hydrogen atom, and $L^1$ is —O—CO—),
(6) a benzyloxymethyl group optionally having substituent(s) (wherein $R^1$ is a phenyl group optionally having substituent(s), $R^2$ and $R^3$ are each a hydrogen atom, and $L^1$ is —O—$CH_2$—),
and the like.

Of these, benzyl group (Bn) optionally having substituent(s), benzyloxycarbonyl group (Cbz) optionally having substituent(s) and benzyloxymethyl group (Bom) optionally having substituent(s) are more preferable, and benzyl group (Bn) optionally having substituent(s) and benzyloxycarbonyl (Cbz) group optionally having substituent(s) are further preferable.

A method of protecting carboxy group, amino group or hydroxy group by protecting group (I) is performed by a known method, for example, the method described in Greene's Protective Groups in Organic Synthesis and the like or a method analogous thereto.

Examples of the protected organic compound include amino acid, amino acid derivative and the like. As used herein, the amino acid means an organic compound having both an amino group and a carboxy group. The amino acid may be any of α-amino acid, β-amino acid, γ-amino acid, δ-amino acid and the like. Of these, α-amino acid is preferable. In addition, the amino acid may be any of L-type and D-type, preferably L-type.

Examples of the amino acid derivative include peptide, amide, ester, urethane compound (R—NH—CO—OR', R and R' are organic groups), urea compound (R—NH—CO—NHR', R and R' are organic groups) and the like. Of these, peptide is preferable. Peptide may be oligopeptide or polypeptide. The "oligopeptide" generally refers to one wherein the number of amino acid residues is not more than 10, and a peptide having more than 10 amino acid residues is called "polypeptide". Of the peptides, one composed of α-amino acid is preferable, and one composed of L-type α-amino acid is more preferable.

A characteristic protected organic compound in the present invention is a protected sulfur-containing organic compound. That is, according to the method of the present invention using halogenated acetic acid, a protected sulfur-containing organic compound can be deprotected by catalytic hydrogenation without using an excess metal catalyst, even if a sulfur atom to be a catalyst poison is present. Examples of the sulfur-containing organic compound include organic compounds having an alkylsulfanyl group, a disulfide bond and the like.

The protected sulfur-containing organic compound is preferably a protected sulfur-containing amino acid and/or a protected sulfur-containing amino acid derivative. Examples of the sulfur-containing amino acid include methionine, cysteine without free sulfanyl group, cystine and the like. More preferred is methionine and/or cystine, and further preferred is methionine. Each of methionine, cysteine and cystine may be L-type or D-type, preferably L-type.

Cysteine having a free sulfanyl group (—SH) shows a strong action of catalyst poison. Therefore, cysteine is preferably cysteine having no free sulfanyl group. Examples of the cysteine without a free sulfanyl group include cysteine wherein hydrogen atom of —SH is substituted by an organic group having one or more carbon number (preferably, sulfanyl-protecting group). Examples of the sulfanyl-protecting group and a protection method using same include known protecting group and protection method described in Greene's Protective Groups in Organic Synthesis and the like.

Examples of the sulfur-containing amino acid derivative include peptide, amide, ester, urethane compound (R—NH—CO—OR', R and R' are organic groups), urea compound (R—NH—CO—NHR', R and R' are organic groups) and the like, which contain an sulfur-containing amino acid residue. Of these, a peptide containing an sulfur-containing amino acid residue is preferable.

[Halogenated Acetic Acid]

The halogenated acetic acid is preferably at least one selected from the group consisting of trichloroacetic acid, dichloroacetic acid, monochloroacetic acid, trifluoroacetic acid, difluoroacetic acid and monofluoroacetic acid, more preferably trifluoroacetic acid.

The amount of halogenated acetic acid to be used is preferably not less than 1 mol, more preferably not less than 2 mol, further preferably not less than 3 mol, per 1 mol of the protected functional group. The amount of halogenated acetic acid to be used does not have an upper limit, and an excess amount of halogenated acetic acid may be used. Halogenated acetic acid may be used as a reaction solvent. When a protected sulfur-containing organic compound is deprotected, to suppress action of catalyst poison of sulfur-containing organic compound to the metal catalyst, the amount of the halogenated acetic acid to be used is preferably not less than 1 mol, more preferably not less than 2 mol, further preferably not less than 3 mol, per 1 mol of the total sulfur atom contained in the protected sulfur-containing organic compound.

[Metal Catalyst]

A known metal catalyst can be used for catalytic hydrogenation. Examples of the metal catalyst include nickel catalyst, copper catalyst, platinum group element (i.e., ruthenium, osmium, rhodium, iridium, palladium, platinum) catalyst and the like.

The metal catalyst may be composed of a metal alone (e.g., palladium black), or may be a metal supported on a carrier. As the carrier, a known one can be used and, for example, activated carbon, silica, alumina, zeolite and the like can be mentioned. Of these, activated carbon is preferable from the aspects of easy availability and the like. From the aspects of catalyst activity, the metal catalyst is preferably one wherein a metal is supported on a carrier.

Examples of the nickel catalyst include Raney-nickel, nickel carbon, silica-supported nickel catalyst, alumina-supported nickel catalyst and the like. Examples of the palladium catalyst include Pearlman's catalyst, Lindlar's catalyst, palladium carbon, silica-supported palladium catalyst, alumina-supported palladium catalyst and the like.

Examples of the copper catalyst include copper-chrome oxide catalyst and the like. Examples of the ruthenium catalyst include ruthenium carbon, silica-supported ruthenium catalyst, alumina-supported ruthenium catalyst and the like. Examples of the rhodium catalyst include rhodium carbon, silica-supported rhodium catalyst, alumina-supported rhodium catalyst and the like. Examples of the platinum catalyst include Adams' catalyst, platinum carbon, silica-supported platinum catalyst, alumina-supported platinum catalyst and the like.

The metal catalyst is preferably at least one selected from the group consisting of nickel catalyst, copper catalyst, ruthenium catalyst, palladium catalyst, rhodium catalyst and platinum catalyst, more preferably palladium catalyst, further preferably palladium carbon wherein palladium(0) is supported on activated carbon.

The amount of a metal catalyst to be used is defined by the metal amount thereof. From the aspects of catalytic activity, cost and the like, a metal amount of a metal catalyst is preferably not less than 10 parts by mass, more preferably not less than 15 parts by mass, further preferably not less than 20 parts by mass, and preferably not more than 50 parts by mass, more preferably not more than 45 parts by mass, further preferably not more than 40 parts by mass, per 100 parts by mass of the protected organic compound. As mentioned above, while the method described in non-patent document 2 uses excess palladium black, halogenated acetic acid is used in the method of the present invention, due to which a protected sulfur-containing organic compound can be deprotected even with a small amount of a metal catalyst.

[Catalytic Hydrogenation]

Catalytic hydrogenation is generally carried out by stirring in a solvent. Examples of the solvent include halogenated acetic acid itself, and solvents other than halogenated acetic acid (hereinafter to be abbreviated as "other solvent") and, for example, water, methanol, ethanol, isopropanol, tetrahydrofuran, hexane, heptane, cyclohexane, ethyl acetate, acetonitrile, acetic acid and the like can be used. As the solvent, halogenated acetic acid alone, or a mixed solvent of halogenated acetic acid and other solvent is preferable, and halogenated acetic acid alone is more preferable.

Catalytic hydrogenation is generally performed at a temperature not less than ambient temperature. In the present invention, the "ambient temperature" means 20° C.±15° C. (i.e., 5-35° C.) as described in JIS Z 8703. To promote catalytic hydrogenation, the temperature thereof is preferably not less than 40° C., more preferably not less than 45° C. On the other hand, the upper limit of the temperature of catalytic hydrogenation determined by the boiling point of the solvent to be used and the like. The temperature of the catalytic hydrogenation is preferably not more than 70° C., more preferably not more than 60° C.

Catalytic hydrogenation is generally performed at a hydrogen pressure not less than the atmospheric pressure. To promote catalytic hydrogenation, the hydrogen pressure is preferably not less than 2 atm, more preferably not less than 3 atm. On the other hand, the upper limit of the hydrogen pressure is determined by the pressure vessel and the like to be used. The hydrogen pressure is preferably not more than 10 atm, more preferably not more than 9 atm.

Catalytic hydrogenation wherein the hydrogen pressure is atmospheric pressure can be performed using, for example, normal-pressure catalytic hydrogenator commercially available from Ishii Laboratory Works CO., LTD., Chemist Plaza CP-100 manufactured by SIBATA SCIENTIFIC TECHNOLOGY LTD. and the like. A hydrogen atmosphere wherein the hydrogen pressure is the atmospheric pressure can also be formed by using a hydrogen balloon. Also, catalytic hydrogenation under pressurization can be performed using, for example, a medium-pressure catalytic hydrogenator commercially available from Ishii Laboratory Works CO., LTD., Chemist Plaza CP-200 manufactured by SIBATA SCIENTIFIC TECHNOLOGY LTD., a portable reactor manufactured by TAIATSU TECHNO CORPORATION, an apparatus composed of a pressurizing apparatus (e.g., hydrogen gas tank) and a pressure vessel in combination and the like.

While the time of catalytic hydrogenation may vary depending on the kind and amount of the protected organic compound and metal catalyst, as well as temperature, hydrogen pressure and the like of catalytic hydrogenation, it is preferably not less than 1 hr, more preferably not less than 16 hr, and preferably not more than 48 hr, more preferably not more than 32 hr.

The deprotection method of the present invention is, for example, useful for the synthesis of peptide (particularly sulfur-containing peptide). In the field of organic synthesis, peptide is often produced by a method including (a) a step of reacting a free amino group of an amino acid having a carboxy group protected by a protecting group or a peptide having the C-terminus protected by a protecting group with a free carboxy group of an amino acid having an amino group protected by a protecting group to give a peptide, (b) a step of forming a free amino group by deprotecting the protected N-terminus of the peptide, (c) a step of repeating the above-mentioned step (a) and step (b) as necessary, and (d) a step of deprotecting all of the C-terminus and N-terminus, which are protected by a protecting group, of the peptide, and the side chain functional group protected by a protecting group.

In the aforementioned production method, when a peptide is produced by using protecting group (I), (1) as a protecting group of at least one functional group selected from the group consisting of carboxy group, amino group and hydroxy group, that the amino acid has, and/or (2) as a protecting group of at least one functional group selected from the group consisting of carboxy group, amino group and hydroxy group, which is at the C-terminus, N-terminus or side chain that the peptide has, the deprotection method of the present invention can be used in one or both of step (b) and step (d).

In the field of organic synthesis, peptide is also produced by a method including (a') a step of reacting a free carboxy group of an amino acid wherein an amino group is protected by a protecting group or a peptide wherein the N-terminus is protected by a protecting group with a free amino group of an amino acid wherein a carboxy group is protected by a protecting group to give a peptide, (b') a step of forming a free carboxy group by deprotecting the protected C-terminus of the peptide, (c') a step of repeating the above-mentioned step (a') and step (b') as necessary, and (d') a step of deprotecting all of the C-terminus and N-terminus, which are protected by a protecting group, of the peptide, and the side chain functional group protected by a protecting group.

In the aforementioned production method, when a sulfur-containing peptide is produced by using protecting group (I), (1') as a protecting group of at least one functional group selected from the group consisting of carboxy group, amino group and hydroxy group, that the amino acid has, and/or (2') as a protecting group of at least one functional group selected from the group consisting of carboxy group, amino group and hydroxy group, which is at the C-terminus, N-terminus or side chain that the peptide has, the deprotection method of the present invention can be used in one or both of step (b') and step (d').

EXAMPLES

The present invention is explained in more detail in the following by referring to Examples, which are not to be construed as limitative, and may be changed within the scope of the present invention.

Example 1: Deprotection of Protected Dipeptide Containing Methionine Residue by Catalytic Hydrogenation

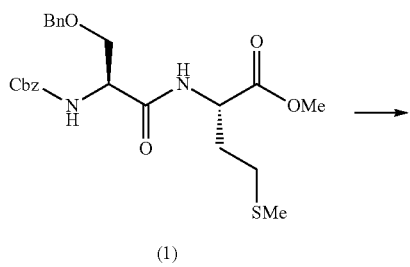

Under a hydrogen atmosphere using Chemist Plaza CP-200 manufactured by SIBATA SCIENTIFIC TECHNOLOGY LTD. (hydrogen pressure 8 atm), the above-mentioned dipeptide (1) (47.5 mg, 0.100 mmol) was stirred in trifluoroacetic acid containing palladium carbon for 24 hr at 50° C. to perform catalytic hydrogenation, whereby the above-mentioned deprotection form (2) (0.0990 mmol, yield: 99%) was obtained.

As palladium carbon, one manufactured by N.E. CHEMCAT CORPORATION having a palladium content of 10 wt % (hereinafter to be described as "10% Pd/C") was used in an amount corresponding to 30 parts by weight (30 wt %) of palladium per 100 parts by weight of the substrate.

Example 2: Deprotection of Protected Dipeptide Containing Methionine Residue by Catalytic Hydrogenation Under a hydrogen atmosphere using a hydrogen balloon, the above-mentioned dipeptide (1) (47.5 mg, 0.100 mmol) was stirred in trifluoroacetic acid containing palladium carbon for 24 hr at ambient temperature to perform catalytic hydrogenation, whereby the above-mentioned deprotection form (2) (0.0992 mmol, yield: 90%) was obtained.

In this Example, 10% Pd/C was used in an amount corresponding to 30 parts by weight (30 wt %) of palladium per 100 parts by weight of the substrate.

Example 3: Deprotection of Protected Dipeptide Containing Methionine Residue by Catalytic Hydrogenation

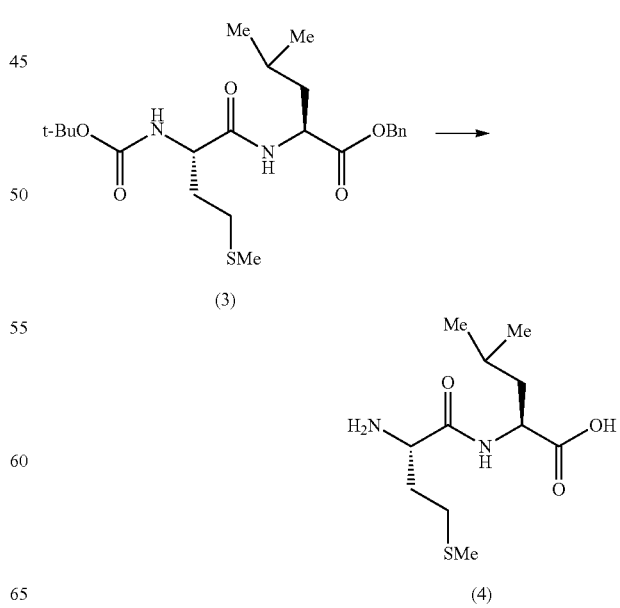

Under a hydrogen atmosphere using a hydrogen balloon, the above-mentioned dipeptide (3) (45.2 mg, 0.100 mmol) was stirred in trifluoroacetic acid containing palladium carbon for 24 hr at 50° C. to perform catalytic hydrogenation, whereby the above-mentioned deprotection form (4) was obtained.

In this Example, 10% Pd/C was used in an amount corresponding to 30 parts by weight (30 wt %) of palladium per 100 parts by weight of the substrate.

Example 4: Deprotection of Protected Oligopeptide Containing Methionine Residue by Catalytic Hydrogenation

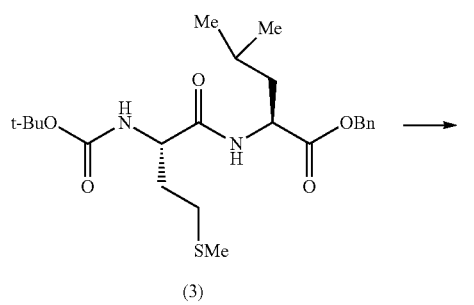

(3)

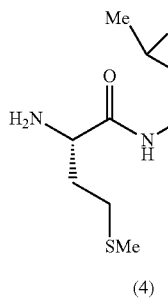

(4)

The above-mentioned dipeptide (3) (45.2 mg, 0.100 mmol) was subjected to catalytic hydrogenation under the same reaction conditions as in Example 2 to quantitatively give the above-mentioned deprotection form (4).

Example 5: Deprotection of Protected Oligopeptide Containing Methionine Residue by Catalytic Hydrogenation

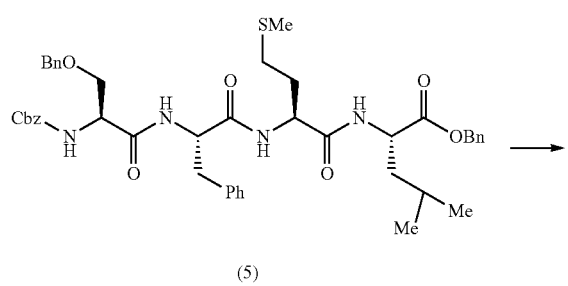

(5)

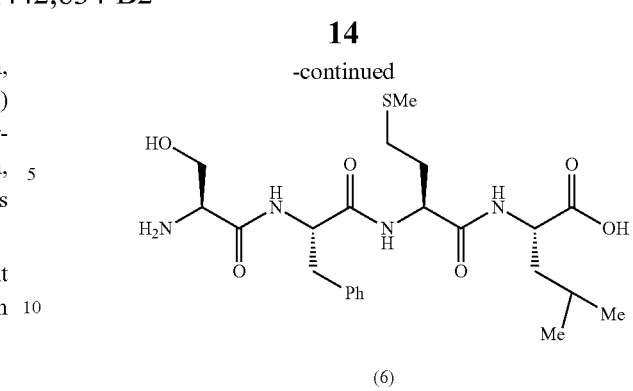

(6)

The above-mentioned oligopeptide (5) (81.1 mg, 0.100 mmol) was subjected to catalytic hydrogenation under the same reaction conditions as in Example 2 to quantitatively give the above-mentioned deprotection form (6).

Example 6: Deprotection of Protected Oligopeptide Containing Methionine Residue by Catalytic Hydrogenation

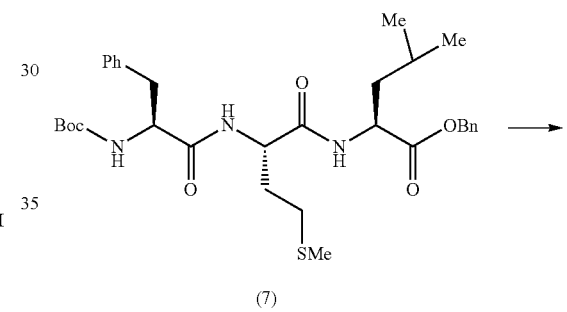

(7)

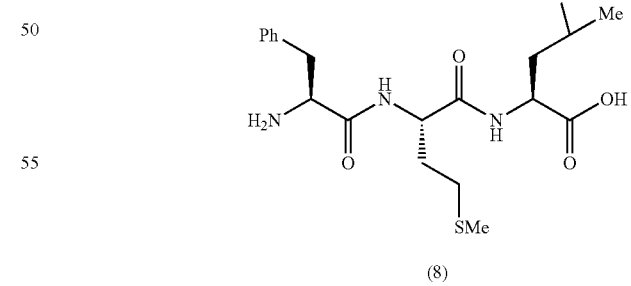

(8)

The above-mentioned oligopeptide (7) (59.9 mg, 0.100 mmol) was subjected to catalytic hydrogenation under the same reaction conditions as in Example 3 to quantitatively give the above-mentioned deprotection form (8) (0.0976 mmol, yield: 98%).

Example 7: Deprotection of Protected Oligopeptide Containing Cystine Residue by Catalytic Hydrogenation

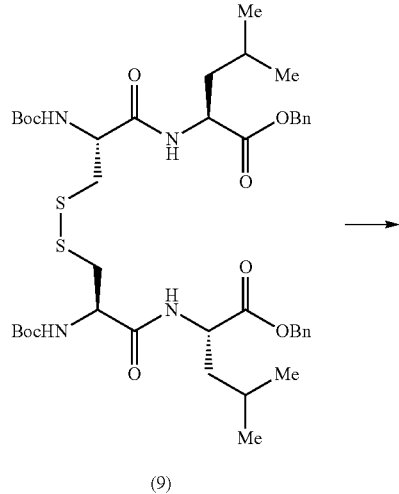

(9)

Under a hydrogen atmosphere at hydrogen pressure of 3 atm, the substrate (9) (84.7 mg, 0.100 mmol) represented by the above-mentioned formula was stirred in trifluoroacetic acid containing 10% Pd/C for 24 hr at 50° C. to perform catalytic hydrogenation, whereby it was confirmed that a carboxy group protected by a benzyl group could be deprotected. In this catalytic hydrogenation, 10% Pd/C was used in an amount corresponding to 30 parts by weight (30 wt %) of palladium per 100 parts by weight of the substrate. In addition, the hydrogen pressure was adjusted using the same apparatus as in Example 1.

Example 8: Deprotection of Protected Methionine by Catalytic Hydrogenation

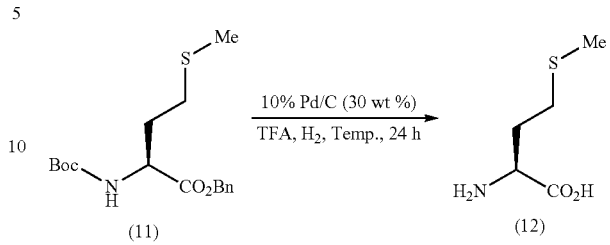

Under a hydrogen atmosphere at hydrogen pressure of 5 atm, protected methionine (11) (33.9 mg, 0.100 mmol) represented by the above-mentioned formula was stirred in trifluoroacetic acid containing 10% Pd/C for 24 hr at ambient temperature to perform catalytic hydrogenation, whereby methionine (12) was quantitatively obtained. Methionine (12) was also quantitatively obtained by catalytic hydrogenation at temperature changed to 50° C. In these catalytic hydrogenations, 10% Pd/C was used in an amount corresponding to 30 parts by weight (30 wt %) of palladium per 100 parts by weight of the protected methionine. In addition, the hydrogen pressure was adjusted using the same apparatus as in Example 1.

Example 9: Deprotection of benzyl 2-chloro-5-(methylthio)benzoate

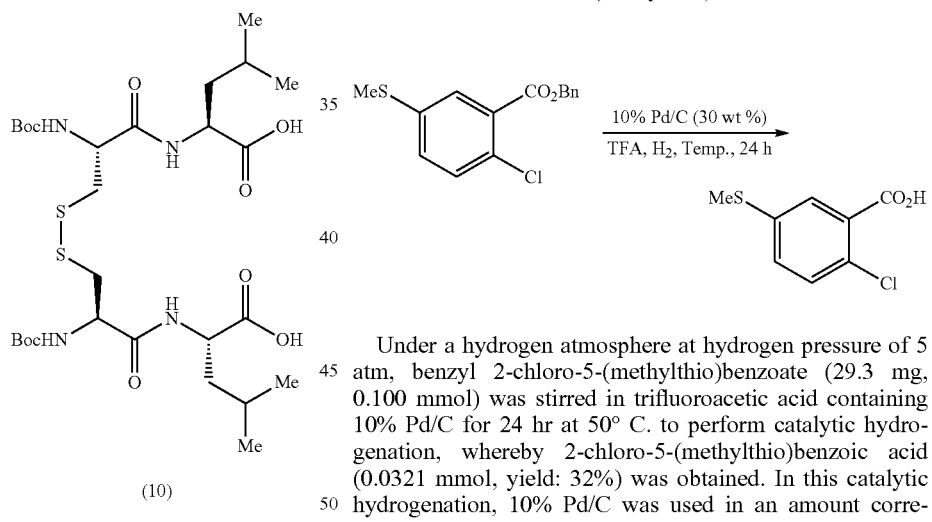

Under a hydrogen atmosphere at hydrogen pressure of 5 atm, benzyl 2-chloro-5-(methylthio)benzoate (29.3 mg, 0.100 mmol) was stirred in trifluoroacetic acid containing 10% Pd/C for 24 hr at 50° C. to perform catalytic hydrogenation, whereby 2-chloro-5-(methylthio)benzoic acid (0.0321 mmol, yield: 32%) was obtained. In this catalytic hydrogenation, 10% Pd/C was used in an amount corresponding to 30 parts by weight (30 wt %) of palladium per 100 parts by weight of benzyl 2-chloro-5-(methylthio)benzoate. In addition, the hydrogen pressure was adjusted using the same apparatus as in Example 1.

Example 10, Comparative Example 1 and Comparative Example 2

Protected oligopeptide (Boc-Ser(Bn)-Ala-Leu-Leu-Arg (NO$_2$)—Ser(Bn)-Ile-Pro-Ala-OBn (SEQ ID NO: 1), 100 mg) was dissolved in the following solvent (3 mL), and 10% Pd/C (0.3 g) was added to the obtained solution. Under a hydrogen atmosphere using a hydrogen balloon, the mixture was stirred at ambient temperature to perform catalytic hydrogenation, whereby deprotection was carried out. The time necessary for completion of the reaction to obtain a deprotected form (H-Ser-Ala-Leu-Leu-Arg-Ser-Ile-Pro-Ala- OH) (SEQ ID NO: 3) after removal of all protecting groups was measured. The results are shown in the following Table 1.

TABLE 1

|  | solvent | reaction completion time |
|---|---|---|
| Example 10 | trifluoroacetic acid | 6.5 hr |
| Comparative Example 1 | methanol | 3 days or more (not completed) |
| Comparative Example 2 | acetic acid | 41 hr |

Example 11 and Comparative Example 3

Protected oligopeptide (H-His(Bom)-Val-Arg($NO_2$)-Gln-His(Bom)-Gly-$NH_2$ (SEQ ID NO: 2), 200 mg) was dissolved in the following solvent, and 10% Pd/C was added to the obtained solution. Under a hydrogen atmosphere using a hydrogen balloon, the mixture was stirred for about 1 day at ambient temperature to perform catalytic hydrogenation, whereby deprotection was carried out. The reaction yield of the deprotected form (H-His-Val-Arg-Gln-His-Gly-$NH_2$) (SEQ ID NO: 4) after removal of all protecting groups was measured by HPLC under the following conditions. The results are shown in the following Table 2.

HPLC conditions
Measurement device: LC-20A manufactured by Shimadzu Corporation
Column: YMC-Pack ODS-A 150×4.6 mM
Measurement temperature: 40° C.
Detection UV wavelength: 220 nm
Mobile phase: mixed solvent of aqueous solution of trifluoroacetic acid (trifluoroacetic acid concentration 0.1% by weight):acetonitrile solution of trifluoroacetic acid (trifluoroacetic acid concentration 0.1 v/v %) (volume ratio at the start of measurement=80:20→□volume ratio after 20 min=20:80)
Flow rate: 1.0 mL/min

TABLE 2

|  | reaction solvent | 10% Pd/C amount | reaction time | reaction yield |
|---|---|---|---|---|
| Example 11 | trifluoroacetic acid (0.5 mL) | 20 mg | 28 hr | 82% |
| Comparative Example 3 | methanol/acetic acid (volume ratio 1/2, 6 mL) | 100 mg | 24 hr | 0.5% |

INDUSTRIAL APPLICABILITY

The method of the present invention using a halogenated acetic acid improves the reaction efficiency of deprotection by catalytic hydrogenation. Particularly, since the action of catalyst poison of a sulfur-containing organic compound to metal catalysts can be suppressed, a protected sulfur-containing organic compound can be efficiently deprotected by catalytic hydrogenation. The method of the present invention is particularly useful for the deprotection of a protected sulfur-containing peptide by catalytic hydrogenation.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of producing a sulfur-containing peptide, comprising:
   (a) reacting:
   (i) a free amino group of an amino acid having a carboxy group protected by a protecting group or a first peptide having a C-terminus protected by a protecting group with
   (ii) a free carboxy group of an amino acid having an amino group protected by a protecting group to obtain a second peptide; and
   (b) deprotecting any C-terminus and N-terminus, which are protected by a protecting group, of said second peptide, to obtain said sulfur-containing peptide,
   wherein said second peptide contains at least one functional group selected from the group consisting of a carboxy group, an amino group, and a hydroxy group, which is protected by a protecting group represented by formula (I):

$$R^1\text{—}C(R^2)(R^3)\text{-}L^1\text{-} \tag{I}$$

wherein $R^1$ is an aryl group optionally having one or more substituent(s), $R^2$ and $R^3$ are each, independently, a hydrogen atom or an aryl group optionally having one or more substituent(s), and $L^1$ is a single bond, —O—CO— or —O—CH$_2$—; and said second peptide contains at least one sulfur-containing amino acid residue selected from the group consisting of methionine, cysteine with protected sulfanyl group, and cysteine, and wherein said method further comprises subjecting said second peptide to hydrogenation in the presence of a metal catalyst and a halogenated acetic acid.

2. The method according to claim 1, wherein said halogenated acetic acid is at least one member selected from the group consisting of trichloroacetic acid, dichloroacetic acid, monochloroacetic acid, trifluoroacetic acid, difluoroacetic acid, and monofluoroacetic acid.

3. The method according to claim 1, wherein said hydrogenation is conducted in the presence of trifluoroacetic acid.

4. The method according to claim 1, wherein said hydrogenation is conducted in the presence of said halogenated acetic acid in an amount of not less than 1 mol per 1 mol of total sulfur atom contained in said sulfur-containing peptide.

5. The method according to claim 1, wherein said metal catalyst is at least one member selected from the group consisting of a nickel catalyst, a copper catalyst, a ruthenium catalyst, a palladium catalyst, a rhodium catalyst, and a platinum catalyst.

6. A method of producing a sulfur-containing peptide, comprising:
(a) reacting:
(i) a free amino group of an amino acid having a carboxy group protected by a protecting group or a first peptide having the C-terminus protected by a protecting group with
(ii) a free carboxy group of an amino acid having an amino group protected by a protecting group to obtain a second peptide;
(b) deprotecting the protected N-terminus of said second peptide, to obtain a third peptide containing an unprotected amino group;
(c) repeating step (a) and step (b) as necessary; and
(d) deprotecting all of the C-terminus and N-terminus, which are protected by a protecting group, of said third peptide, to obtain said sulfur-containing peptide,
wherein said third peptide contains at least one functional group selected from the group consisting of a carboxy group, an amino group, and a hydroxy group, which is protected by a protecting group represented by formula (I):

$$R^1-C(R^2)(R^3)-L^1- \quad (I)$$

wherein said $R^1$ is an aryl group optionally having one or more substituent(s), $R^2$ and $R^3$ are each, independently, a hydrogen atom or an aryl group optionally having one or more substituent(s), and $L^1$ is a single bond, —O—CO— or —O—CH$_2$—; and
said third peptide contains at least one sulfur-containing amino acid residue selected from the group consisting of methionine, cysteine with protected sulfanyl group, and cysteine, and
wherein third method further comprises subjecting said third peptide to hydrogenation in the presence of a metal catalyst and a halogenated acetic acid.

7. The method according to claim 6, wherein said halogenated acetic acid is at least one member selected from the group consisting of trichloroacetic acid, dichloroacetic acid, monochloroacetic acid, trifluoroacetic acid, difluoroacetic acid, and monofluoroacetic acid.

8. The method according to claim 6, wherein said hydrogenation is conducted in the presence of trifluoroacetic acid.

9. The method according to claim 6, wherein said hydrogenation is conducted in the presence of said halogenated acetic acid in an amount of not less than 1 mol per 1 mol of total sulfur atom contained in said sulfur-containing peptide.

* * * * *

UNITED STATES PATENT AND TRADEMARK OFFICE
CERTIFICATE OF CORRECTION

PATENT NO. : 10,442,834 B2
APPLICATION NO. : 14/873517
DATED : October 15, 2019
INVENTOR(S) : Hironao Sajiki et al.

Page 1 of 1

It is certified that error appears in the above-identified patent and that said Letters Patent is hereby corrected as shown below:

In the Specification

Column 3, Line 37, "cystine with protected" should read --cysteine with protected--

In the Claims

Column 20, Line 67, "and cysteine, and" should read --and cystine, and--

Column 22, Line 18, "and cysteine, and" should read --and cystine, and--

Signed and Sealed this
Twenty-fourth Day of November, 2020

Andrei Iancu
*Director of the United States Patent and Trademark Office*